United States Patent [19]
Hyman et al.

[11] Patent Number: 5,217,355
[45] Date of Patent: Jun. 8, 1993

[54] TWO-CYCLE PERISTALTIC PUMP WITH OCCLUSION DETECTOR

[75] Inventors: Oscar E. Hyman, Encinitas; Ahmadmahir M. Moubayd, San Diego; Larry L. Wilson, Poway, all of Calif.

[73] Assignee: IMED Corporation, San Diego, Calif.

[21] Appl. No.: 741,112

[22] Filed: Aug. 5, 1991

[51] Int. Cl.⁵ ............................................. F04B 43/08
[52] U.S. Cl. ...................................... 417/474; 417/479
[58] Field of Search ........................ 417/474, 478, 479

[56] References Cited

U.S. PATENT DOCUMENTS

| | | | |
|---|---|---|---|
| 2,420,148 | 5/1947 | Ostergren | 177/351 |
| 2,770,703 | 11/1956 | Scheurich | 201/63 |
| 2,885,520 | 5/1959 | Giovanni | 201/63 |
| 3,218,864 | 11/1965 | Schugt | 73/497 |
| 3,505,634 | 4/1970 | Von Vick | 338/4 |
| 3,518,033 | 6/1970 | Anderson | 417/478 |
| 3,778,195 | 12/1973 | Bamberg | 417/474 |
| 3,866,473 | 2/1975 | Teitelbaum et al. | 73/398 |
| 4,199,307 | 4/1980 | Jassawalla | 417/474 |
| 4,273,121 | 6/1981 | Jassawalla | 128/214 |
| 4,277,226 | 7/1981 | Archibald | 417/38 |
| 4,306,460 | 12/1981 | Sakurai et al. | 73/721 |
| 4,309,908 | 1/1982 | Rapp et al. | 73/720 |
| 4,345,476 | 8/1982 | Singh | 73/720 |
| 4,346,705 | 8/1982 | Pekkarinen et al. | 128/214 |
| 4,382,753 | 5/1983 | Archibald | 417/479 |
| 4,468,219 | 8/1984 | George et al. | 604/66 |
| 4,479,797 | 10/1984 | Kobayashi et al. | 604/153 |
| 4,526,574 | 7/1985 | Pekkarinen | 604/52 |
| 4,561,830 | 12/1985 | Bradley | 417/474 |
| 4,617,014 | 10/1986 | Cannon et al. | 614/67 |
| 4,650,469 | 3/1987 | Berg et al. | 604/131 |
| 4,657,490 | 4/1987 | Abbott | 417/478 |
| 4,725,205 | 2/1988 | Cannon | 417/477 |
| 4,728,265 | 3/1988 | Cannon | 417/474 |
| 4,836,752 | 6/1989 | Burkett | 417/474 |
| 4,840,542 | 6/1989 | Abbott | 417/9 |
| 4,869,646 | 9/1989 | Gordon | 417/474 |
| 4,967,940 | 11/1990 | Blette | 417/474 |
| 5,017,059 | 5/1991 | Davis | 417/474 |
| 5,055,013 | 10/1991 | Faeser | 417/474 |
| 5,074,756 | 12/1991 | Davis | 417/479 |
| 5,092,749 | 3/1992 | Meijer | 417/479 |

FOREIGN PATENT DOCUMENTS

| | | |
|---|---|---|
| 0090440 | 5/1983 | European Pat. Off. . |
| 3413437 | 4/1985 | European Pat. Off. ............ 417/474 |
| 0374618 | 6/1990 | European Pat. Off. . |
| 0422855A1 | 4/1991 | European Pat. Off. . |

Primary Examiner—Richard A. Bertsch
Assistant Examiner—Peter Korytnyk
Attorney, Agent, or Firm—Nydegger & Associates

[57] ABSTRACT

A linear peristaltic pump for pumping fluid through a resilient tube has a pair of pumping fingers, a pair of pinching fingers, and a strain gauge to monitor pressure inside the tube. The first pumping finger squeezes the tube at a first location, and the second pumping finger squeezes the tube at a second location. Additionally, the first pumping finger is configured and operated to displace approximately twice the fluid volume displaced by the second pumping finger. The first pinching finger occludes the tube upstream to the first pumping finger and the second pinching finger occludes the tube between the first and second pumping fingers. To monitor dimensional changes in the outer diameter of the tube and thereby indicate pressure inside the tube, the strain gauge is mounted on the pump between the second pinching finger and first pumping fingers. Finally, a leaf spring and photoelectric sensor are associated with the first pumping finger to indicate when the finger is in its fully withdrawn position.

23 Claims, 4 Drawing Sheets

TWO-CYCLE PERISTALTIC PUMP WITH OCCLUSION DETECTOR

FIELD OF THE INVENTION

The present invention pertains to fluid pumps. More specifically, the present invention pertains to peristaltic pumps which sequentially squeeze a resilient tube to force fluid through the tube. The present invention is particularly, but not exclusively, useful as a pump for the infusion of medical solutions to a patient.

BACKGROUND OF THE INVENTION

Over the years there have been a number of pumps developed for infusion of medical solutions to patients. Such pumping of fluids has been routinely accomplished through a wide variety of well known pumping mechanisms. In the administration of fluids to a patient, it is desirable that the pump be of the "non-wetting" variety, such as that exemplified by the well known peristaltic pump. A peristaltic pump is a type of pump which uses wave-like motion against the walls of a flexible tube containing the fluid being pumped. The non-wetting-type pump is particularly useful in hospital and medical situations in that the fluid being pumped is not subject to contamination through direct contact with the component parts of the pump. In like fashion, if corrosive fluids are being pumped there is no direct contact of corrosive fluid with component parts of the pump.

Another desirable characteristic of pumping mechanisms in general is for the pump to deliver fluid at a rate which remains reasonably constant. In other words, throughout the pumping cycle, the rate of flow should remain substantially steady, without any surges or significant variations in the flow rate.

Peristaltic pumps of the non-wetting variety are basically of two types, namely rotary peristaltic pumps or linear peristaltic pumps. One disadvantage of rotary peristaltic pumps, however, is that they have relatively poor efficiency. In addition, they impose high shear and tension stresses on the tubing which is used to convey the fluid. Another disadvantage is that because of the high forces typically produced by rotary peristaltic pumps, the tubing eventually experiences spalling of its inner walls. There is also, after a period of time, permanent plastic deformation, or "set", of the tubing. In other words, the tubing's normally circular cross section becomes flattened into a more oval shape.

Linear peristaltic pumps, in comparison, typically use reciprocating parts to provide peristaltic action against the flexible tube in order to move the fluid through the tube. Such peristaltic pumps consist of a plurality of reciprocating pumping fingers, typically twelve (12), that are sequentially urged against the tube to occlude adjacent segments of tubing in wave-like action. Although linear peristaltic pumps overcome some of the above-stated disadvantages associated with rotary peristaltic pumps, they do so at considerable added cost and with the greater complexity added by the mechanism needed to properly synchronize twelve (12) pumping fingers. Since the pumping fingers are urged to sequentially occlude adjacent segments of tubing, the crushing forces imposed on the tubing and fluid are comparable to those encountered with rotary peristaltic pumps. There is less damage, however, than that caused by rotary peristaltic pumps, because the occlusion forces are localized to the area beneath each finger rather than being applied in movement along the whole length of the tubing. Nonetheless, even with a linear peristaltic pump, there is still some damage such as plastic deformation of the tubing. As a consequence, the structural integrity of the tube carrying the fluid is compromised and as the tubing assumes a progressively more oval cross-sectional shape, the volume and flow rate of the fluid delivered in each pumping cycle is affected.

Furthermore, in order to smooth the pumping transition from one cycle to the next, some linear peristaltic pumps have what is called a "wrap" cycle. During a "wrap" cycle, the motor driving the pump is accelerated to quickly move the upstream finger into occlusion. Thereafter, the motor can resume normal speed to sequentially squeeze and occlude adjacent portions of the tube in its wave-like cycle action. Incorporating this "wrap" cycle can require use of a relatively complicated and expensive motor and motor drive circuit with high acceleration capability. Also, because fluid is not delivered during this "wrap" cycle, most linear peristaltic pumps use many fingers (e.g. twelve (12) additional pumping fingers, as mentioned earlier) to minimize the proportionate time of the "wrap" cycle. Maintaining proper alignment and relational movement between such a plurality of fingers also deteriorates the reliability of operation of the device and increases manufacturing costs.

Apart from the specific type of pump being used, and independent of the number of fingers configured in the design of the pump, it is desirable that some means for monitoring fluid pressure within the tube be provided. By so monitoring fluid tube pressure, unwanted systems occlusions, flow blockages, or leaks may be quickly detected and attended to. Moreover, the pump being used can be programmed to react to changes in fluid pressure when fluid pressure is known, in order to provide automatic response to the types of pumping system irregularities discussed above. One example of a peristaltic pump which incorporates a pressure sensor is disclosed in U.S. Pat. No. 4,617,014, issued to Cannon. In particular, the Cannon apparatus incorporates a strain gauge assembly with a twelve-finger peristaltic pump for monitoring fluid pressure upstream and downstream of the pump. The strain gauge is used for providing automatic pump control signals in response to fluid pressure in the IV line. The importance of fluid pressure monitoring is underscored by the fact that several other proposals have also been made for monitoring fluid pressure in an IV line of a peristaltic pump. For example, one other such system which correlates changes in the outside diameter of an IV line to fluid pressure within the line is disclosed in U.S. Pat. No. 4,836,752 to Burkett. Like the apparatus disclosed in Cannon, Burkett also uses a strain gage pressure sensor assembly which reacts to changes in the outer diameter of an IV tube to generate control signals which correspond to fluid pressure.

Accordingly, it is an object of the present invention to provide a peristaltic pump of the non-wetting type which is simple and efficient in operation. It is another object of the present invention to provide a peristaltic pump which results in reduced stresses on the fluid-carrying tube and thus longer tube life. It is yet another object of the present invention to provide a peristaltic pump which produces a substantially linear, and non-pulsing flow for the fluid being pumped. A further object of the present invention is to provide a peristaltic pump which has fluid pressure monitoring capabilities. Still another object of the present invention is to provide a peristaltic pump which is relatively easy to manufacture, durable and reliable in its operation and comparatively cost-effective.

SUMMARY OF THE INVENTION

A preferred embodiment of the peristaltic pump for pumping fluid through a resilient tube comprises a base, a platen mounted on the base for holding the tube, a strain gauge for sensing pressure in the tube, and four (4) fingers mounted on the base engageable with the tube. The four (4) fingers include, in sequence downstream, a first pinching finger, a first pumping finger, a second pinching finger, and a second pumping finger. The fingers are mounted reciprocally on the base to urge against the tube between a withdrawn position and an extended position. The first pumping finger squeezes the tube to displace a fluid volume which is approximately twice the fluid volume displaced by the second pumping finger.

A drive mechanism moves the first pumping finger toward its extended position as the second pumping finger is moved toward its withdrawn position. The drive mechanism further moves the first pumping finger toward its withdrawn position as the second pumping finger is moved toward its extended position. The first pinching finger occludes the tube upstream from the first pumping finger as the first pumping finger moves toward its extended position. The second pinching finger occludes the tube between the first and second pumping fingers, as the second finger moves toward its extended position.

In one embodiment, the first pumping finger displaces twice the fluid as the second pumping finger because it is twice as large as the second pumping finger. In another embodiment, the first pumping finger displaces twice the fluid by traveling a distance which is approximately twice that of the distance traveled by the second pumping finger.

The peristaltic pumping device also includes a strain gauge pressure sensor which measures changes in the outer diameter of the IV tube to monitor pressure inside the tube. In particular, the strain beam of the gauge is mounted on a pressure finger which is positioned against the tube between the first pumping finger and the second pinching finger. The strain gauge is thereby located intermediate the pinching fingers. Thus, as the pinching fingers of the pump alternately squeeze their respective sections of tube, the strain gauge is capable of respectively monitoring pressure in the tube either upstream or downstream of the strain beam.

Additionally, a photoelectric detector is mounted on the base next to the first pumping finger. When this first pumping finger fully retracts from the IV tube, the drive mechanism of the finger urges against a leaf spring, which has an attached flag. The flag on the leaf spring is consequently moved to block the light path of the detector and thereby generate a signal which indicates that the finger has been properly retracted during the pumping cycle.

The novel features of this invention, as well as the invention itself, both as to its structure and its operation, will be best understood from the accompanying drawings, taken in conjunction with the accompanying description, in which similar reference characters refer to similar parts, and in which:

DETAILED DESCRIPTION OF THE PREFERRED EMBODIMENTS

Figure 1:
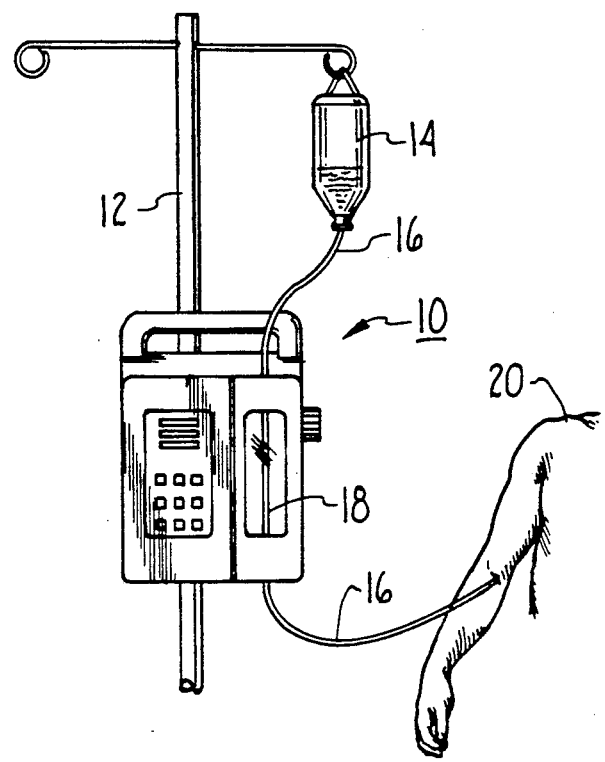
FIG. 1 shows the peristaltic pump in its intended environment.

Referring now to FIG. 1, there is shown a peristaltic pump apparatus, generally designated 10, shown in use in its intended environment. In particular, peristaltic pump apparatus 10 is shown attached to an intravenous (I.V.) pole 12 on which a fluid source 14 containing an I.V. fluid is held. Fluid source 14 is connected in fluid communication with a hollow resilient tube 16. Tube 16 is a conventional I.V. infusion-type tube typically used in a hospital or medical environment, and is made of any type of flexible tubing, such as polyvinylchloride (PVC). A portion 18 of flexible tube 16 is mounted in operative engagement with pumping apparatus 10, for pumping fluid through tube 16 into a patient's arm 20.

Figure 2:
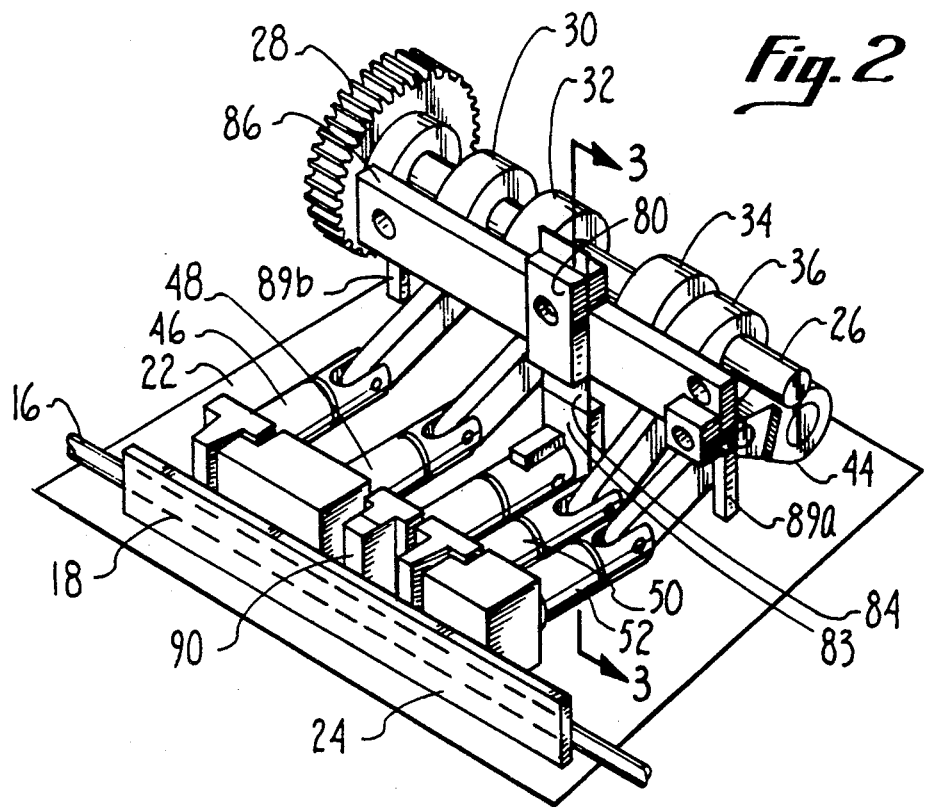
FIG. 2 is a perspective view of one embodiment of the peristaltic pumping mechanism together with an associated pump drive mechanism.

The components of peristaltic pump apparatus 10 can be best appreciated with reference to FIG. 2, where it will be seen that peristaltic pump apparatus 10 includes a base 22 which has a generally flat platen 24. Platen 24 provides a surface against which portion 18 (shown in phantom in FIG. 2) of tube 16 may be occluded.

Mounted on base 22 is a rotatable shaft 26, which is driven by a motor (not shown) that engages with gear 28. Shaft 26 also includes cams 30, 32, 34 and, 36. Each cam 30, 32, 34 and 36 contacts a corresponding linkage. Only linkage 44, which is associated with cam 36, is shown in FIG. 2. The cams 30, 32, 34 and 36 against the respective linkages and thereby drive pump fingers 46, 48, 50, and 52, respectively. While any suitable pump drive mechanism may be used to drive fingers 46, 48, 50, and 52, the particular pump drive mechanism shown in FIG. 2 provides certain advantages over conventional drive mechanisms.

As disclosed above, the four (4) fingers 46, 48, 50 and 52 are reciprocally mounted on base 22 for being urged against tube portion 18. To provide further protection for tube portion 18, and to keep dirt and other unwanted materials from the inner workings of the peristaltic pump 10, a flexible membrane (not shown) may be connected to base 22 and over or between the fingers 46, 48, 50, 52 and tube portion 18. Each finger 46, 48, 50, 52 is reciprocally mounted to move back and forth with respect to platen 24. Each finger 46, 48, 50, 52 is movable between a withdrawn position, or upper limit, and an extended position, or lower limit, to deform tube portion 18 a specified amount as explained hereinafter.

Figure 4:
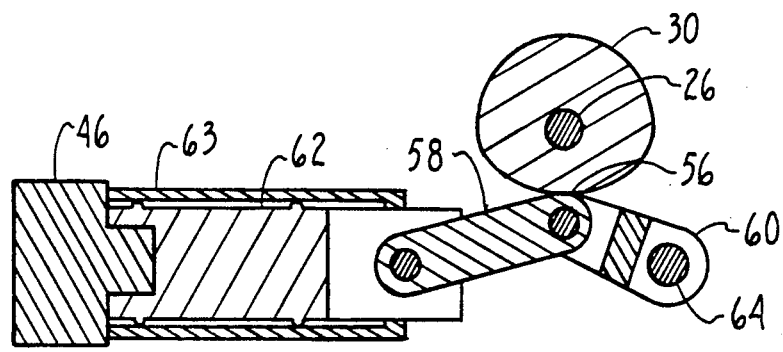
FIG. 4 is a cross-sectional view of one finger linkage of the pump drive mechanism in the fully withdrawn position.
Figure 5:
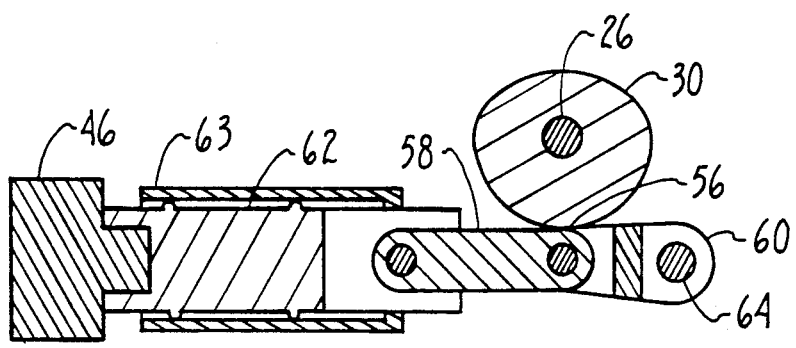
FIG. 5 is a cross-sectional view of one finger linkage of the pump drive mechanism in the fully extended position.

In particular, pinching fingers 46 and 50 are of identical configuration, and serve as pinch valves. Fingers 46 and 50 are movable between a withdrawn position as shown in FIG. 4, and an extended position as shown in FIG. 5. Taking a single finger 46 as an example, as can be appreciated with reference to FIGS. 4 and 5, rotation of shaft 26 causes corresponding rotation of shape-formed cam 30. Cam 30 is positioned on shaft 26 to urge against an elbow 56, which is formed between drive link 58 and pivot link 60. Drive link 58 is pivotally attached to drive member 62, which is in turn fixedly attached to finger 46. Similarly, pivot link 60 is pivotally attached to a pivot shaft 64. Moreover, drive member 62 is constrained to substantially linear motion by guide 63. Accordingly, the rotary motion of drive shaft 26 is transformed by the cam/link arrangement described above to translational reciprocation of finger 46.

It will be understood that each of the fingers 46, 48, 50, and 52 is actuated by a drive mechanism similar to the one just described. As can be appreciated from the disclosure above, and again referring to finger 46 as an example, the reciprocating motion of finger 46 causes it to alternately press against and withdraw from tube portion 18. Finger 46 thereby alternately occludes and opens tube portion 18. In particular, with respect to fingers 46 and 50 these, fingers 46, 50 are positioned so that the smallest possible motion of fingers 46, 50 suffices to alternately occlude or open tube portion 18 to allow fluid to flow beneath them. In other words, when fingers 46, 50 are in an open or fully withdrawn position, as shown in FIG. 4, an aperture is provided in tube portion 18 which is sufficient for relatively unrestricted flow of fluid beneath finger 46 or 50. Typically, the extent of the range of motion of pinching fingers 46 and 50 is fixed at no more than one (1) to three (3) times the wall thickness of the tube portion 18. Thus, first finger 46 and third finger 50 are essentially pinching fingers.

It may also be readily appreciated with reference to FIG. 2 that second finger 48 and fourth finger 52 are pumping fingers in the sense that it is these fingers which squeeze, but do not completely occlude, tube portion 18 to urge fluid out of tube portion 18. In addition, first pumping finger 48 has a unique configuration and is designated as a "large" pumping finger. Finger 52 is also of a unique configuration and designated as a "small" pumping finger.

With respect to the description of the invention herein, "large" and "small" describe pumping fingers which are constructed to move against tube portion 18 such that the amount of fluid displaced as "large" finger 48 moves downward against tube 18, is approximately two (2) times that displaced by an equal reciprocal downward motion of "small" finger 52. It is important to note that the reciprocal motion of fingers 48 and 52 is generally equal in range, but that in the fully extended position, the pumping fingers 48, 52 do not ever fully occlude the tubing. Instead, they squeeze the flexible tube portion 18 from a relatively larger percent of initial tubing outside diameter to a relatively smaller percent of initial tubing outside diameter. It is to be understood that the fingers 48, 52 are driven by mechanisms such as the mechanism described above for driving finger 46.

The preferred embodiment of the present invention also includes a gauge assembly 80 which is associated with peristaltic assembly 10 substantially as shown in FIG. 2. A more detailed description of the gauge assembly 80 itself, however, can best be obtained with cross-reference to FIGS. 2 and 3.

Figure 3:
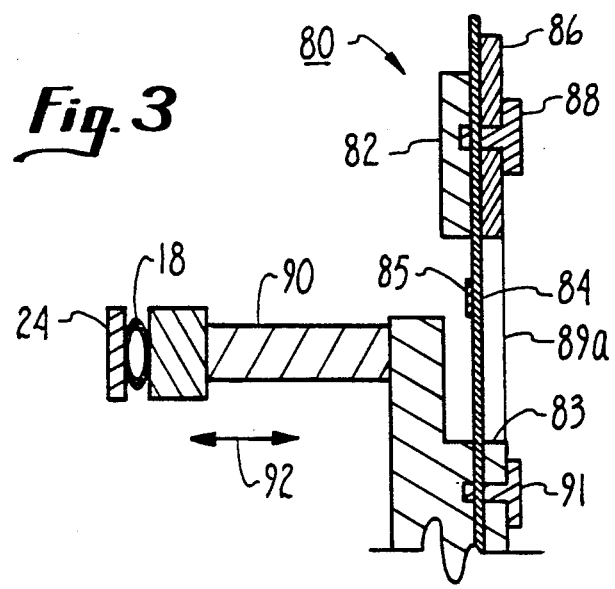
FIG. 3 is a side cross-sectional view of the strain gauge assembly of the peristaltic pump as seen along the line 3—3 in FIG. 2, with portions broken away for clarity, shown in its relationship with the fluid tubing and the base of the peristaltic pump.

In FIG. 3 the gauge assembly 80 is shown in cross-section and is seen to include a top mounting block 82 and a bottom mounting block 83. A cantilevered strain beam 84 is mounted on block 83. On the surface of cantilevered strain beam 84 is a strain gauge 85. The entire assembly which includes block 82, block 83, strain beam 84, and the strain gauge 85 can be of a type similar to model no. X1680 manufactured by Transducers, Inc. 14030 Bolsa Lane, Cerritos, California 90701.

A mounting plate 86 is also shown which holds strain beam 84 against block 82. More particularly, a bolt 88 is shown which passes through block 82 and beam 84, and is threadably engaged with plate 86 to hold beam 84 against block 82. Mounting block 82 is shown mounted on extensions 89a and b. Extensions 89a and b, as perhaps best shown in FIG. 2, are in turn mounted by any suitable means to base 22. Fixedly attached to cantilevered strain beam 84 at the end opposite from its connection to mounting block 82 is a pressure transmitting finger 90. In reference to FIGS. 2 and 3, it may be seen that finger 90 is positioned to physically interconnect cantilevered strain beam 84 and tube portion 18. More specifically, beam 84 is held against finger 90 by block 83, which is attached to beam 84 and finger 90 by bolt 91. As will be appreciated by reference to FIGS. 2 and 3, upon engagement of I.V. tube 16 with device 10, a portion 18 of tube 16 is positioned between platen 24 and the pressure transmitting finger 90, which is connected with the cantilevered strain beam 84. Thus, as the diameter of tube portion 18 varies, the position of pressure transmitting finger 90 is also varied. Consequently, as finger 90 moves, strain beam 84 is deflected. The deflections of strain beam 84 are in turn sensed by the strain gauge 85.

Figure 9:
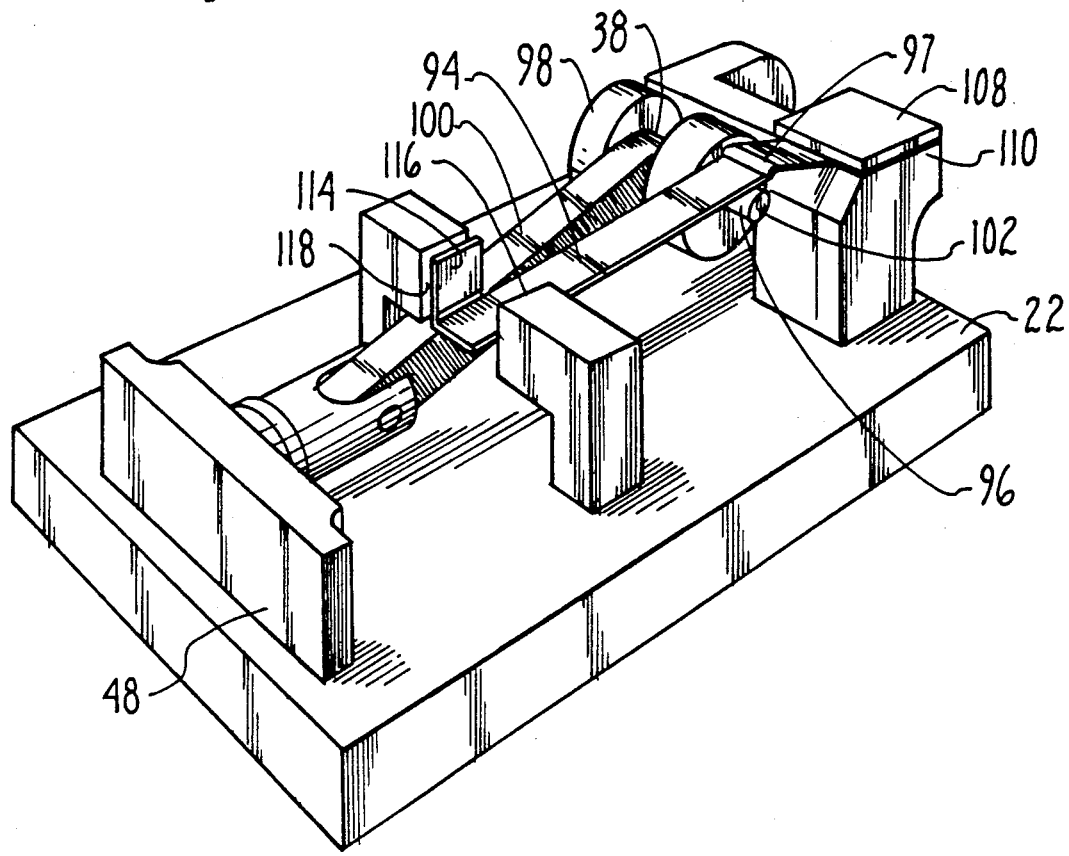
FIG. 9 is an isometric view of the large pumping finger and leaf spring of the present invention.
Figure 10:
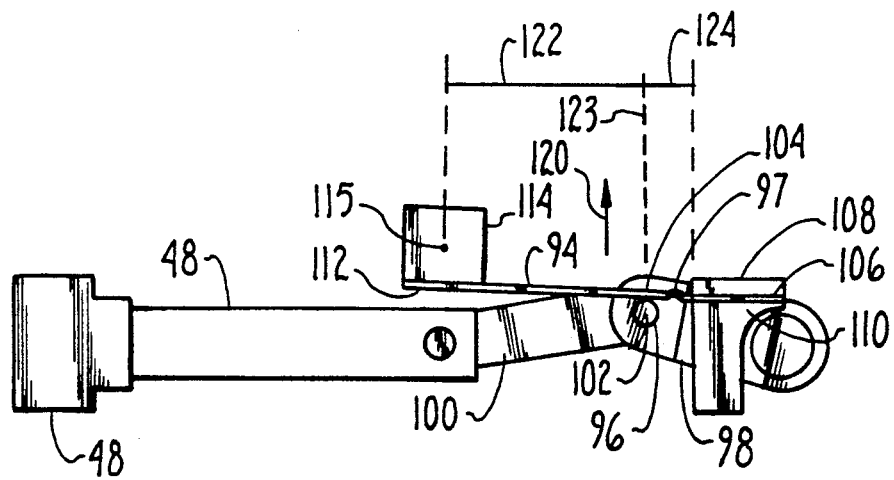
FIG. 10 is a side view of the large pumping finger and leaf spring of the present invention, with the photoelectric sensor removed for clarity.

Turning now to FIGS. 9 and 10, the large pumping finger 48 is shown in operative association with a leaf spring 94. As will be discussed further below, leaf spring 94 is deflected when large pumping finger 48 is urged into its fully withdrawn position by fluid pressure inside tube portion 18. It is necessary for pumping finger 48 to be urged into its fully withdrawn position in order for apparatus 10 to function properly. Thus, leaf spring 94 provides an indication of the proper functioning of apparatus 10. More particularly, link pin 96, which interconnects pivot link 98 with drive link 100 of linkage 38, is formed with an extension 102. When finger 48 is in its fully withdrawn position, extension 102 of link pin 96 urges against leaf spring 94 at point 104 (shown in FIG. 10) of spring 94. Leaf spring 94 is itself fixedly clamped at its end 106 between upper support 108 and lower support 110. Support 110 is in turn mounted on base 22. Near its fixed end 106, leaf spring 96 is formed with a stress relief section 97, as best seen in FIG. 10. At the free end 112 of leaf spring 94, a flag 114 is formed or attached to leaf spring 94. Flag 114 is any material that is opaque to light. More particularly, flag 114 is material that can block light which is transmitted by photoelectric transmitter 116 to photoelectric receiver 118 during operation of leaf spring 94 to be subsequently disclosed.

Figure 6:
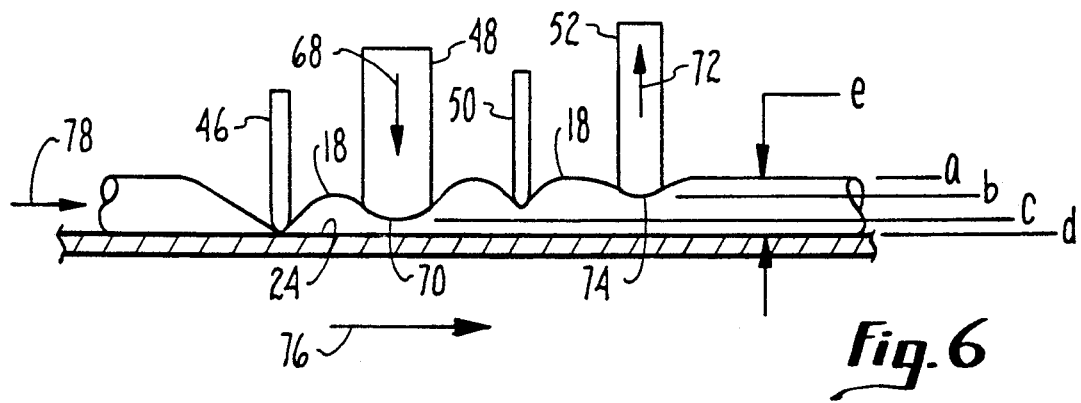
FIG. 6 is a schematic illustration of operation of the peristaltic pump shown in FIG. 2.
Figure 7:
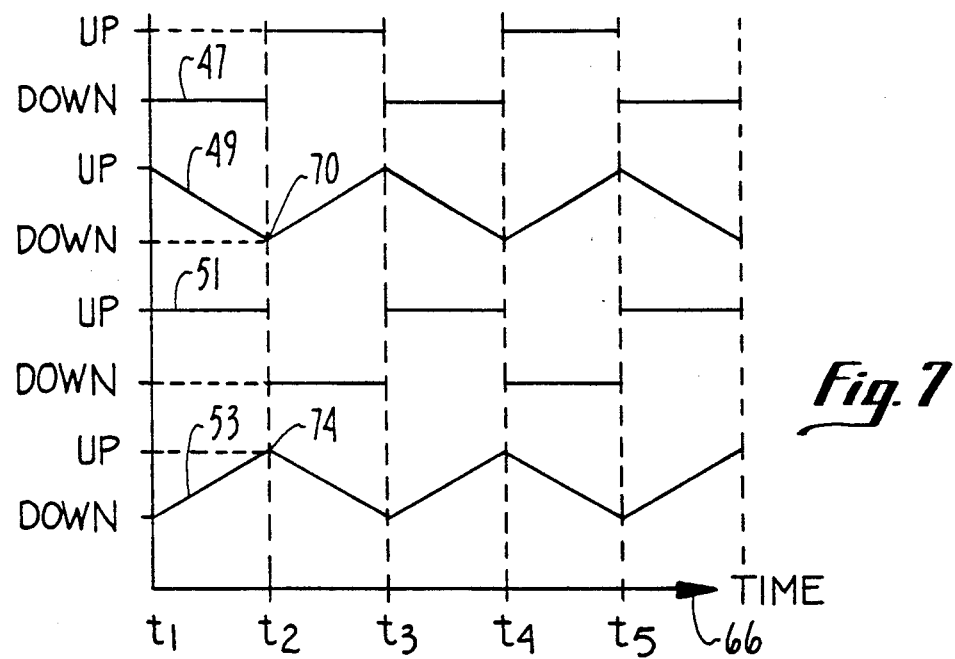
FIG. 7 is a schematic diagram illustrating the relative operation of the movement of fingers utilized in operation of the peristaltic pump in accordance with the present invention.

Operation of the present invention may perhaps be best appreciated with reference to FIGS. 6 and 7. In particular, FIG. 6 represents relative movement of fingers 46, 48, 50 and 52. In FIG. 7, the relative movement of pinching fingers 46 and 50 and pumping fingers 48 and 52, represented by motion curves 47, 49, 51, and 53, respectively, are shown in relation to one another over a period of time that includes reference points $t_1$, $t_2$, $t_3$, $t_4$ and $t_5$ on time line 66. Cams 30, 32, 34, and 36 are initially oriented on drive shaft 26 and subsequently rotated on drive shaft 26 to operate the linkage system described above so that fingers 46, 48, 50 and 52 are reciprocated to execute in the present embodiment a two-cycle motion as shown in FIGS. 6 and 7. The first cycle is between time $t_1$ and $t_2$, and the second cycle is between $t_2$ and $t_3$.

In the first cycle, finger 46 is held closed in its fully extended position, while finger 50 is held in its fully withdrawn or open position, as shown in FIG. 6. This is indicated in FIG. 7 by motion curve 47 at starting point time $t_1$. At point t as shown in FIG. 6 finger 46 is in the down position and finger 50 is in the up position. As cams 30, 32, 34, and 36 are rotated, fingers 46 and 50 initially remain in the same position, but fingers 48 and 52 begin to move. Finger 48 moves down in the direction as shown by arrow 68, having started at upper limit or height elevation "b" and moving down to lower limit or elevation "c". Thus, in FIG. 6, finger 48 is shown at its position 70, and is shown in FIG. 7 by motion curve 49 to be in a fully extended position, yet not occluding tube section 18. Thus, immediately prior to $t_2$, finger 46 is still down. At the same time, finger 52, which started in its down position at elevation "c" at time $t_1$, has moved up as shown by arrow 72 to position 74 immediately prior to time $t_2$. Thus, finger 48 having moved downward from its extreme retracted position at elevation "b" toward platen 24, drives fluid out and toward patient 20 generally in the direction of exit arrow 76. Simultaneously, finger 52 has started moving upward from its extreme extended position, as shown by motion curve 53 in FIG. 7 between time $t_1$ and $t_2$. The difference in the size of the fingers, i.e. "large" versus "small" results in a net delivery of fluid comparable to that resulting from the displacement produced by the "small", finger acting alone. In other words, because the "large" finger 48 displaces twice the volume as that of "small" finger 52, the net result of cycle one is the delivery of one unit of volume toward the exit of tube 16 as shown by arrow 76.

As cycle one is concluding at time $t_2$, the "large" finger 48 and "small" finger 52 have exchanged vertical positions. Also at time $t_2$, pinching fingers 46 and 50 exchange positions. Pinching finger 46 is raised toward its fully withdrawn position as shown at elevation point "c", and pinching finger 50 is lowered as shown by elevation line "d". Because pinching finger 50 is now closed, and pinching finger 46 is open, fluid is drawn into the tubing 16, and, thus, portion 18 as shown by entry arrow 78. The rate of flow of fluid into the entrance of tube section 18 is twice that of the output rate, since finger 48 displaces twice as much fluid as finger 52. Then, while finger 48 is retracting between time $t_2$ and $t_3$, finger 52 is extending from elevation "b" to elevation "c" as shown in FIG. 6. This produces a net delivery output of one unit of fluid via exit arrow 76.

This action progresses until time $t_3$ at which time cycle two has been completed. At time $t_3$, the pinching fingers 46, 50 again revert so that pinching finger 46 is again down and pinching finger 50 is again up so that they are essentially in position 70 at point in time $t_1$. The system at point $t_3$ is then in the same state it was at time $t_1$. Times $t_4$ and $t_5$ are merely repetitions of an additional cycle.

It is important to note that the speed with which the pumping fingers move toward the tubing during a cycle ideally is not constant. As the tubing is squeezed, equal increments of motion result in a displacement of progressively larger amounts of fluid. In other words, linear reciprocal motion of the finger against the tube as the tube becomes more compressed results in faster flow of fluid out from under the deformed tubing. To accommodate this, the ideal motion of pumping fingers 48 and 52 is such that each finger moves toward the tubing at a relatively rapid pace and then progressively slows as the tubing becomes more deformed. The benefit of such motion is a uniform rate of fluid flow forced by the squeezing action of the respective fingers.

Thus, the pumping mechanism having two cycles as described herein is a highly efficient apparatus for effecting fluid displacement. It also provides a linear, non-pulsatile flow of fluid which is desired in peristaltic pumping apparatus. In addition, this design allows the use of much smaller motors than would be necessary with either conventional linear or rotary peristaltic pumps. Because the size of the motor required generally reflects the peak rather than the average load encountered, the combined mechanism disclosed herein redistributes the load reflected so that the motor has a reduced peak. Further, the required occlusion is produced by two small pinching fingers that do not displace significant amounts of volume or distort the metering portion of the tubing. On the other hand, the pumping fingers, unlike conventional peristaltic fingers, never completely occlude the tubing or "crush" the tubing to produce undesired results.

It is also important to note that the present invention avoids waste of energy in linear and rotary peristaltic conventional pumps. The great bulk of such motive energy is typically consumed in heating the tubing through the high compressive and shear forces applied. This is because, as mentioned earlier, the fingers must not only pump but also occlude the tube. The present invention, however, separates the functions of pumping and occluding. Thus, the present invention has removed the need for such repeated mashing and deformation of tubing to occlude it by the pumping aspect. In particular, the plastic set, or deformation, from repeated smashing of tubing does not affect the accuracy of the present apparatus. Any "set" around the area beneath the pinching fingers 46, 50 is much narrower because such fingers are much narrower and have the specific function of occluding the tube. However, the wider area under the wider pumping fingers 48 and 52 do not significantly experience the "set" phenomenon because they are not required to fully occlude the tubing. In other words, the pumping fingers 48, 52 have an upper and lower pumping finger limit as shown by the dimensions "b" and "c" in FIG. 6. The pinching fingers 46 and 50, however, have a shorter motion to fully occlude the inside diameter "e" of the tube between finger heights "a" and the platen height "d".

In accordance with the discussion above, the fingers 46, 48, 50, 52 are urged into their respective extended positions by their respective profiled cams 30, 32, 34, 36, which are in turn driven, through drive shaft 26, by a motor (not shown). On the other hand, fingers 46, 48, 50, 52 are urged back into their respective retracted or withdrawn positions by the resilient elastomeric force of fluid-filled tube portion 18. It is sometimes the case, however, that the force which causes the fingers to retract, i.e., the elastomeric force of tube portion 18, may occasionally be insufficient to urge one or more of the fingers 46, 48, 50, 52 into their fully withdrawn positions. This can occur, for example, when the portion 18 becomes materially fatigued during a prolonged period of use. It is necessary, however, for the fingers 46, 48, 50 to fully retract for apparatus 10 to deliver fluid at the desired rate. Thus, it is important to monitor for the proper retraction of fingers 46, 48, 50 to ensure that apparatus 10 is functioning properly.

To this end, it is to be appreciated that gauge assembly 80 can be positioned to determine dimensional differences in the outer diameter of tube section 18 to determine whether second pinching finger 50 has fully withdrawn. As seen in FIG. 3, tube section 18 is located directly between platen 24 and pressure transmitting finger 90. During the pumping of fluid through tube section 18, the outer diameter of tube section 18 will vary, depending upon the fluid pressure within tube section 18. This variation in pressure will cause a consequent variation in the distance between transmitting finger 90 and platen 24 on respectively opposite sides of the center portion of tube section 18. It will be appreciated by those skilled in the pertinent art that this change in dimension can be correlated to changes in the fluid pressure within the tube section 18. As will be further appreciated by those skilled in the art, a variation in the outer diameter of tube section 18 and the consequent change in distance between finger 90 and platen 24 will cause a motion of pressure transmitting finger 90 generally in the directions indicated by the arrow 92. Further, it will be appreciated that the movement of pressure transmitting finger 90 in either of the directions indicated by arrow 92 will be manifested as a fluctuation of the cantilevered strain beam 84. With a strain gauge 85 mounted on cantilevered strain beam 84, the fluctuations of beam 84 can be electronically measured and transmitted for further processing.

Turning now to FIGS. 9 and 10, the operation of leaf spring 94 can be seen. As the following discussion will disclose, the function of leaf spring 94, in combination with photoelectric transmitter 116 and receiver 118, is to sense when first pumping finger 48 reaches its fully withdrawn position. More particularly, when first pumping finger 48 is in its fully withdrawn position, pivot link 98 and, consequently, extension 102 of link pin 96 have moved to the highest position in the cycle, relative to base 22. At this point in its cycle, extension 102 of link pin 96 urges against leaf spring 94 and causes it to deflect upward, in the direction of arrow 120, as shown in FIG. 10. This causes flag 114, which is attached to spring 94, to also move upward in the direction of arrow 120. As it does so, flag 114 interrupts the light path between photoelectric transmitter 116 and photoelectric receiver 118.

The magnitude of the upward motion of flag 114 will be the distance that point 104 of leaf spring 94 is deflected upward, times the ratio of distance 122 (from the center 115 of flag 114 to the vertical line 123 which passes through point 104) to distance 124 (from line 123 to upper support 108). Thus, when first pumping finger 48 is fully withdrawn, the photoelectric light path described above is interrupted. In the event that first pumping finger 48 does not fully retract to its withdrawn position, extension 102 of pin 96 does not urge flag 114 upward far enough to block the photoelectric light path. Accordingly, when first pumping finger 48 is not fully retracted to its withdrawn position, the light path between transmitter 116 and receiver 118 is not interrupted.

Electronics (not shown) are also associated with photoelectric receiver 118 to accordingly indicate cycles of first pumping finger 48 during which finger 48 does not fully retract. More particularly, one complete cycle of finger 48 lasts for a known time period. Consequently, if finger 48 fully retracts, the light path to photoelectric receiver 118 should be interrupted once during that period. In the event that finger 48 does not fully retract, this fact will be sensed by receiver 118 in that the light path between receiver 118 and transmitter 116 will not be interrupted during the appropriate time period. Accordingly, receiver 118 could be electrically connected to an appropriate alarm (not shown) to indicate the fact that finger 48 did not fully retract to its withdrawn position during a period of time which corresponds to one complete pumping cycle. Furthermore, in order to reduce the likelihood of false alarms, it may be desirable that an alarm occur only after a predetermined number of pumping finger 48 cycles has elapsed without interruption of the photoelectric light path described above.

As the skilled artisan will recognize, the monitoring capability provided by the above-disclosed leaf spring photoelectric sensor, in combination with the capability provided by the strain gauge sensor, provides a means for determining whether or not apparatus 10 is delivering fluid at an acceptable flow rate. More particularly, as stated above, unwanted reductions in flow rate through tube 16 can occur if the elastomeric force of resilient tube 16 fails to urge any one of the fingers 46, 48 or 50 into its respective fully withdrawn position. On the other hand, substantially no reduction in flow will occur in the event that second pumping finger 52 fails to fully retract to its withdrawn position. This is because second pumping finger 52 affects only flow continuity through tube 16, and not overall flow rate. More specifically, even in its fully extended position, finger 52 does not completely occlude tube 16. Accordingly, only the proper operation of fingers 46, 48, 50 must be monitored to determine whether apparatus 10 is delivering fluid at the desirable rate.

To this end, therefore, strain beam 84 provides an indication of proper second pinching finger 50 operation, while photoelectric receiver 118 provides indication of the proper operation of first pinching finger 46 and first pumping finger 48. More specifically, strain beam 84 can sense abnormally high pressure in tube portion 18. Abnormally high pressure in tube portion 18 indicates that second pinching finger 50 has not fully retracted to its withdrawn position and that tube portion 18 accordingly remains partially occluded by finger 50. Therefore, in such an instance, tube portion 18 will become over pressurized when first pumping finger 48 fully extends into tube portion 18. Likewise, as disclosed above, photoelectric receiver 118 directly senses whether finger 48 has fully retracted to its withdrawn position. Additionally, photoelectric receiver 118 provides an indirect indication of first pinching finger 46 failing to fully retract to its withdrawn position. When first pinching finger 46 fails to fully retract, first pinching finger 46 continues to partially occlude tube 16. Thus, the portion of tube 16 which is directly compressed by first pumping finger 48 cannot be completely filled with fluid, in accordance with well known principles of fluid flow, at a rate which is sufficient to urge finger 48 into the fully retracted position. Stated differently, when finger 46 does not fully retract, the resulting decreased elastomeric force of tube 16 against first pumping finger 48 is insufficient to urge first pumping finger 48 from its extended position into its fully withdrawn position. In accordance with the above disclosure, photoelectric receiver 118 can cause an alarm to activate to indicate improper finger 48 operation, in this case caused by improper first pinching finger 46 operation. Such an alarm thereby alerts the operator of apparatus 10 that improper flow conditions exist through apparatus 10.

Figure 8:
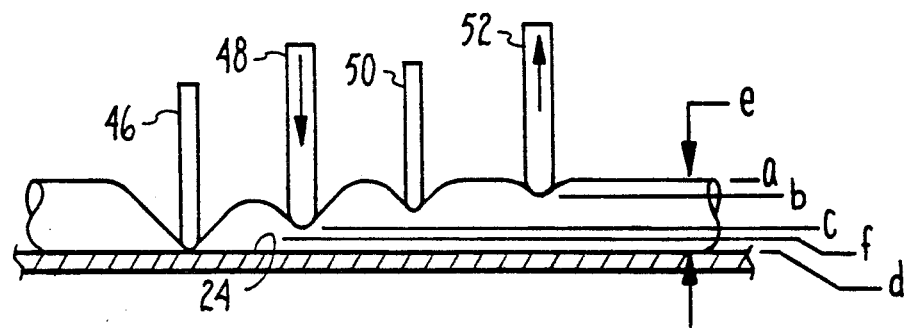
FIG. 8 is a schematic illustration of an alternative embodiment of the peristaltic pump in accordance with the present invention.

Finally, with reference to FIG. 8, there is shown schematically an alternative embodiment representative of the present invention in which pumping fingers 48 and 52 are of identical size. The associated drive members 62, however, are arranged such that the pumping fingers 48 and 52, being of the same size, are directed through a different amount of travel, respectively. In particular, it can be seen that while the limited travel of reciprocation of finger 52 is between elevations "b" and "c" as shown in FIG. 8, the limited travel of reciprocation of finger 48 is between "b" and "f". The distance between "b" and "f" is a larger distance and thus there is a larger amount of travel. Provided such travel is accomplished during the same period of time, finger 48 thus displaces more fluid. By properly choosing the amount of travel and deformation of tubing involved, the amount of travel can thus be adjusted so that finger 48 squeezes tube 18 to displace a fluid volume that is approximately twice the fluid volume displaced by the squeezing movement of finger 52.

While the particular two-cycle peristaltic pump as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A device for pumping fluid through a resilient tube which comprises:
    a base;
    a platen mounted on said base for holding said tube;
    means mounted on said base for alternately squeezing said tube against said platen at a first and second location;
    means mounted on said base for alternately occluding said tube upstream from said first location and between said first and second locations, said first location being squeezed as said tube is occluded upstream from said first location;
    a strain gauge mounted on said base and operatively coupled with said tube at a third location thereon, for sensing fluid pressure in said tube at a first time when said tube downstream from said third location is open and at a second time when said tube upstream from said third location is open;
    photoelectric sensor means attached to said base for indicating a position of said squeezing means as it is pushed outwardly to a withdrawn position; and
    the pressure sensor operating in combination with the position sensor to provide a means for determining whether the device is delivering fluid at an acceptable rate.

2. A device for pumping fluid through a resilient tube as recited in claim 1 wherein said squeezing means comprises a first pumping finger reciprocally mounted on said base to urge against said tube at said first location with movement between a withdrawn position and an extended position, and a second pumping finger reciprocally mounted on said base to urge against said tube at said second location with movement between a withdrawn position and an extended position.

3. A device for pumping fluid through a resilient tube as recited in claim 2 wherein said first pumping finger squeezes said tube to displace a fluid volume that is approximately twice the fluid volume displaced by the squeezing movement of said second finger.

4. A device for pumping fluid through a resilient tube as recited in claim 3 wherein said first pumping finger contacts an area of said tube that is approximately twice as large as the area of said tube contacted by said second pumping finger.

5. A device for pumping fluid through a resilient tube as recited in claim 3 wherein between their respective withdrawn and extended positions, said first pumping finger travels a distance which is approximately twice the distance traveled by said second pumping finger.

6. A device for pumping fluid through a resilient tube as recited in claim 5 wherein said tube has a lumen with a selected inner diameter and said distances traveled by said first pumping finger and said second pumping finger between their respective said withdrawn position and said extended position is less than said selected inner diameter.

7. A device for pumping fluid through a resilient tube as recited in claim 1 wherein said second location is squeezed as said tube is occluded between said first and second locations.

8. A device for pumping fluid through a resilient tube as recited in claim 1 wherein said occluding means comprises a first pinching finger for occluding said tube upstream from said first location and a second pinching finger for occluding said tube between said first and second locations.

9. A device for pumping fluid through a resilient tube as recited in claim 8 wherein said gauge mounted for operative engagement with said strain tube intermediate said first pumping finger and said second pinching finger.

10. A device for pumping fluid through a resilient tube as recited in claim 1 wherein said gauge is synchronized with said squeezing means to establish said first and second times.

11. A device for pumping fluid through a resilient tube which comprises:
    a base;
    a platen mounted on said base and adapted to hold said tube;
    a first pumping finger reciprocally mounted on said base to urge against said tube with movement between a withdrawn position and an extended position;
    a second pumping finger reciprocally mounted on said base to urge against said tube with movement between a withdrawn position and an extended position;

means for moving said first pumping finger toward its said extended position as said second pumping finger is moved toward its said withdrawn position and moving said first finger toward its said withdrawn position as said second finger is moved toward its said extended position;

a first valve mounted on said base for occluding said tube upstream from said first pumping finger as said first pumping finger moves toward its extended position;

a second valve mounted on said base for occluding said tube between said first and second pumping fingers as said second finger moves toward its extended position;

a strain gauge mounted on said base and operatively associated with said tube to alternately measure the outside diameter of said tube at a first time when said tube downstream from said gauge is occluded and at a second time when said tube upstream from said gauge is occluded;

a photoelectric sensor for indicating a position of said first pumping finger as it is pushed outwardly to a withdrawn position; and the pressure sensor operating in combination with the position sensor to provide a means for determining whether the device is delivering fluid at an acceptable rate.

12. A device for pumping fluid through a resilient tube as recited in claim 11 wherein said first pumping finger squeezes said tube to displace a fluid volume that is approximately twice the fluid volume displaced by the squeezing movement of said second pumping finger.

13. A device for pumping fluid through a resilient tube as recited in claim 12 wherein said first pumping finger is approximately twice as large as said second pumping finger.

14. A device for pumping fluid through a resilient tube as recited in claim 12 wherein between their respective withdrawn and extended positions, said first pumping finger travels a distance which is approximately twice the distance traveled by said second pumping finger.

15. A device for pumping fluid through a resilient tube as recited in claim 14 wherein said tube has a lumen with a selected inner diameter and said distances traveled by said first pumping finger and said second pumping finger between their respective said withdrawn position and said extended position is less than said selected inner diameter.

16. A device for pumping fluid through a resilient tube as recited in claim 11 wherein said strain gauge is mounted for operative engagement with said tube intermediate said first pumping finger and said second valve.

17. A device for pumping fluid through a resilient tube as recited in claim 16 wherein said gauge is synchronized with said squeezing means to establish said first and second times.

18. A method for pumping fluid through a resilient tube which comprises the steps of:
mounting said tube on a platen;
alternately squeezing said tube at a first location using a first pumping finger and at a second location using a second pumping finger;
alternately occluding said tube upstream from said first location, and between said first and second locations;
monitoring the fluid pressure at a fixed location of said tube with a strain gauge operatively coupled with said tube between said first and second locations, said strain gauge monitoring said pressure at a first time when said tube downstream of said gauge is open and at a second time when said tube upstream of said gauge is open;
sensing a location of said first pumping finger using a photoelectric device; and
operating the pressure sensor in combination with the position sensor to provide a means for determining whether the device is delivering fluid at an acceptable rate.

19. A method for pumping fluid through a resilient tube as recited in claim 18 wherein said step of squeezing said tube at said first location is accomplished while said tube is occluded upstream from said first location.

20. A method for pumping fluid through a resilient tube as recited in claim 19 wherein said step of squeezing said tube at said second location is accomplished while said tube is occluded between said first and second locations.

21. A method for pumping fluid through a resilient tube as recited in claim 18 wherein said first location is squeezed to displace approximately twice the fluid volume displaced when said second location is squeezed.

22. A method for pumping fluid through a resilient tube as recited in claim 18 wherein said tube remains patent at said first and second locations.

23. A method for pumping fluid through a resilient tube as recited in claim 18 further comprising the step of indicating when said tube upstream of said gauge is not fully expanded.

* * * * *